United States Patent
Breedveld

(10) Patent No.: US 8,144,833 B2
(45) Date of Patent: Mar. 27, 2012

(54) PLANNING FOR ADAPTIVE RADIOTHERAPY

(75) Inventor: Sebastiaan Breedveld, Rotterdam (NL)

(73) Assignee: Elekta AB (publ), Stockholm (SE)

( * ) Notice: Subject to any disclaimer, the term of this patent is extended or adjusted under 35 U.S.C. 154(b) by 186 days.

(21) Appl. No.: 12/763,530

(22) Filed: Apr. 20, 2010

(65) Prior Publication Data

US 2011/0255665 A1   Oct. 20, 2011

(51) Int. Cl.
*A61N 5/10* (2006.01)
(52) U.S. Cl. ......................................... 378/65
(58) Field of Classification Search .................. 378/65
See application file for complete search history.

(56) References Cited

U.S. PATENT DOCUMENTS 7,593,505 B2   9/2009  Saracen et al.

FOREIGN PATENT DOCUMENTS

EP            1238684 A1   9/2002

OTHER PUBLICATIONS

Craft D and Bortfeld T, 2008 "How many plans are needed in an IMRT multi-objective plan database?", published in Phys. Med. Biol. 53, 2785-96).

Monz M, Küfer K H, Bortfeld T R and Thieke C 2008 "Pareto Navigation-algorithmic foundation of interactive multi-criteria IMRT planning", Phys. Med. Biol. 53, 985-98.

Haimes Y Y, Lasdon L S and Wismer D A (1971) "On a bicriterion formulation of the problems of integrated system identification and system optimization", IEEE Trans. Man Cybern. 1 296-7.

Wilkens, J.J., Alaly J.R., Zakarian K., Thorstad W.L. and Deasy J.O., 2007, "IMRT treatment planning based on prioritizing prescription goals", Phys. Med. Biol. 52 1675-92.

Jee K-W, McShan D.L. and Fraas B.A., 2007, "Lexicographic ordering: intuitive multicriteria optimization for IMRT", Phys. Med. Biol. 52 1845-61.

Breedveld et al "The equivalence of multi-criteria methods for radiotherapy plan optimization", 2009 Physics in Medicine and Biology vol. 54, pp. 7199-7209.

Breedveld et al "A novel approach to multi-criteria inverse planning for IMRT" 2007 Physics in Medicine and Biology, vol. 52, pp. 6339-6353.

*Primary Examiner* — Courtney Thomas
(74) *Attorney, Agent, or Firm* — Westerman, Champlin & Kelly, P.A.; Z. Peter Sawicki

(57) ABSTRACT

The present invention provides a method for updating and optimizing a treatment plan for radiotherapy. An initial treatment plan, calculated using a constraint-driven method, may be updated using a weighted-sum method, where Lagrange multipliers generated in the constraint method are reused as the weights for the weighted sum. This method results in acceptable updated treatment plans that are generated in a small fraction of the time taken to generate an entirely new treatment plan, reducing patient discomfort and ensuring the radiotherapy facility can treat more patients.

12 Claims, 1 Drawing Sheet

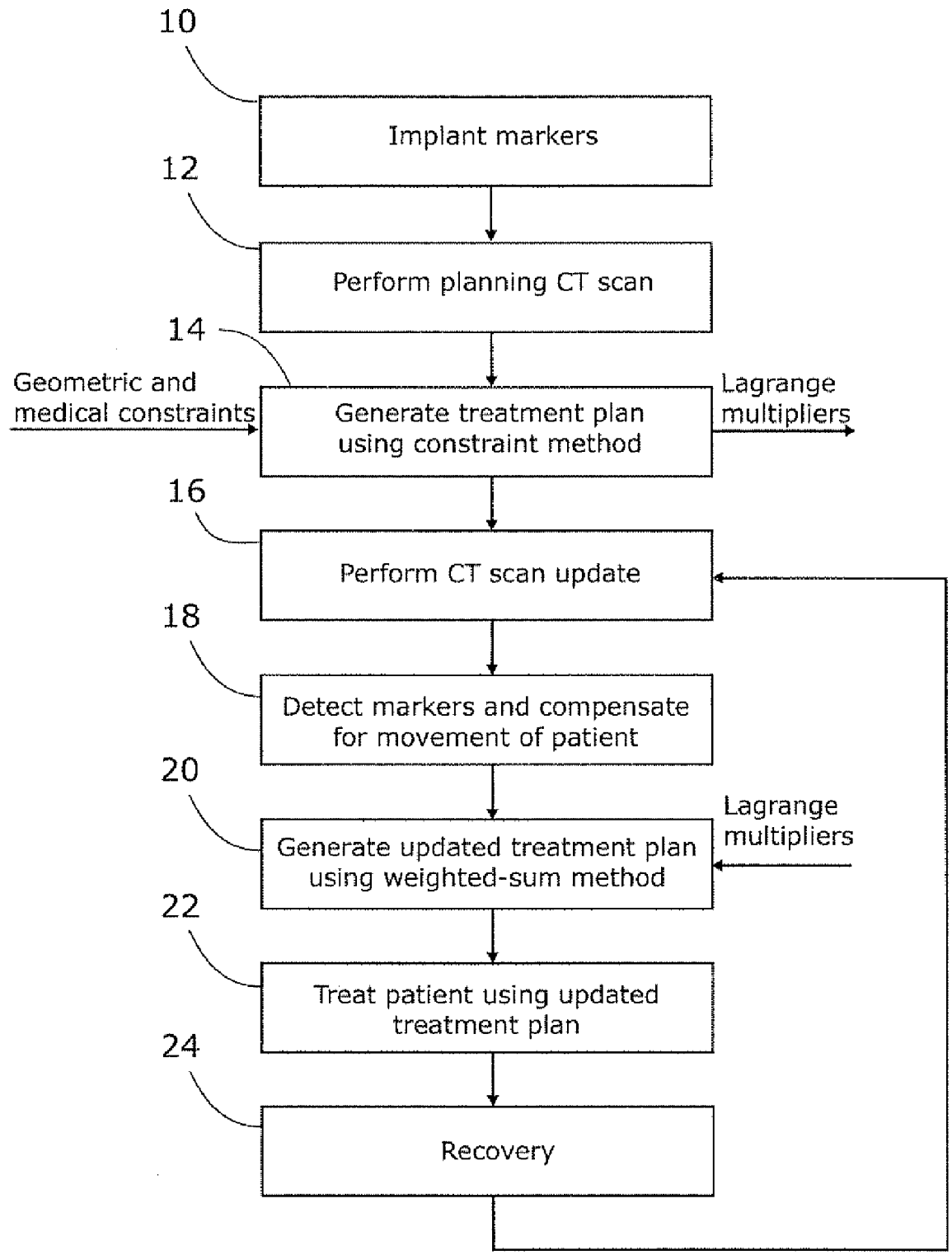

PLANNING FOR ADAPTIVE RADIOTHERAPY

FIELD OF THE INVENTION

The present invention relates to the field of radiation therapy, or radiotherapy, and particularly relates to a method that allows a radiotherapy treatment plan to be updated more easily.

BACKGROUND ART

Prior to beginning a course of radiotherapy, volumetric images of the patient, and specifically the target region, need to be obtained so that a plan for the treatment can be constructed. The aim of the treatment plan is to establish how to apply the radiotherapy to the patient so that the target region receives the desired, lethal dose, whilst the surrounding healthy tissue receives as little dose as possible.

Radiotherapy is often delivered by a linear accelerator-based system, which produces a beam of high-energy x-rays and directs this toward a patient. The patient typically lies on a couch or patient support, and the beam is directed toward the patient from an offset location. During treatment, the beam source is rotated around the patient while keeping the beam directed toward the target point (the "isocentre"). The result is that the isocentre remains in the beam at all times, but areas immediately around the isocentre are only irradiated briefly by the beam during part of its rotation. By positioning (for example) a tumour at the isocentre, the dose to the tumour is maximised whilst the dose to surrounding healthy tissue is reduced.

In addition, the cross-section of the beam can be varied by way of a range of types of collimator, such as the so-called "multi-leaf collimator" (MLC) illustrated in EP 0,214,314. These can be adjusted during treatment so as to create a beam whose cross-section varies dynamically as it rotates around the patient.

Other aspects of the radiotherapy apparatus can also be varied during treatment, such as the speed of rotation of the source and the dose rate. Thus, there are a large number of variables offered by the apparatus in order to tailor the radiation dose that is delivered to the patient.

The volumetric images are therefore analysed to identify a target region into which a minimum dose is to be delivered, any sensitive regions such as functional organs for which a maximum dose must be observed, and other non-target regions into which the dose is to be generally minimised. This three-dimensional map must then be used to develop a treatment plan, i.e. a sequence of source movements, collimator movements, and dose rates which result in a three-dimensional dose distribution that (a) meets the requirements as to maximum and minimum doses (etc) and (b) is physically possible, e.g. does not require the source to rotate around the patient faster than it is physically capable.

This can be expressed as a mathematical problem in which the overall dose to healthy tissue must be minimised, subject to constraints as to the maximum dose to sensitive regions, the minimum dose to the target, and the various machine constraints such as the maximum rotation speeds, possible MLC shapes, etc. Although complex, the mathematical problem can be solved by one of a range of techniques (with varying efficiency) but this does require significant computing time.

In addition, courses of radiotherapy are usually fractionated. That is, they usually comprise several cycles of a short period of therapy (known as a fraction) followed by a recovery period. Unhealthy tissue (i.e. that which is the target of the therapy) takes longer than healthy tissue to recover from each dose of radiation. Therefore, by managing the therapeutic dose that is delivered in each fraction, as well as the length of the recovery period between each fraction, the unhealthy tissue can gradually be destroyed while the healthy tissue survives.

As a course of radiotherapy can last several weeks or longer, it is possible if not likely that the target region will move and/or change shape during the course of the treatment. This can mean that the original treatment plan becomes ineffective, as it was based on a different three-dimensional pattern of regions. The consequence of this is that the target tissue may receive a lower dose than intended and healthy tissue may receive a higher dose than desired. To counteract this, new images of the patient and target region can be taken before the start of each fraction, and the treatment plan recalculated to compensate for any movement of the target region.

It is preferable for this inter-fraction imaging to take place with the patient in the same position as they will be in during treatment. To that end, the patient needs to stay in the same position during imaging, during the period while the treatment plan is being updated, and also during the course of the treatment. This can be some time, increasing the potential discomfort of the patient. A reduction in the time taken to complete this process would be beneficial both to the patient and to the facility operating the radiotherapy apparatus, who could then treat more patients than before in the same period of time.

U.S. Pat. No. 7,593,505 discloses a method in which a library of previously accepted treatment plans is used to speed up creation of a new treatment plan at the start of the planning process. European patent EP1238684 discloses a method in which the treatment plan is updated before each fraction by combining new image information with an existing approved plan for the same patient. However, both of these methods still take a relatively long time to compute.

SUMMARY OF THE INVENTION

The present invention seeks to remedy the problems associated with the prior art by providing an improved (i.e. faster) method for updating treatment plans between fractions.

Treatment plan generation is a predominantly automated process, to reduce the time required. However, even with full automation the process (referred to as 2-phase $\epsilon$-constraint, or 2p$\epsilon$c) is still time-consuming. During the initial planning period a number of iterations can be required until the optimum plan is obtained. The original dose distribution problem has constraints imposed by the maximum doses receivable by the tissues surrounding the target.

In mathematical optimisation, only one objective is minimized at a time. The multi-criteria (i.e. there is more than one objective or criterion) $\epsilon$c method optimises one objective at a time, constrains it to the optimal value found, and then minimises the next objective. The 2p$\epsilon$c method is similar, but optimises each objective to a defined goal rather than its optimal value.

One method for solving constrained problems like these is to convert them into "unconstrained optimisation" problems. By combining the objective and constraints a function is formed, known as a Lagrangian. The different constraints are weighted by "Lagrange multipliers". The Lagrangian is a saddle-shaped function defined by the normal variable (i.e. x) and the Lagrange multipliers (i.e. $\lambda$). The optimal solution of this function is the saddle point defined by a unique x (optimal solution for the constrained objective) and λ (the Lagrange multipliers).

For the final result of the constrained optimisation problem, the obtained Lagrange multipliers are generally not important. However, if the multi-criteria optimisation is written as a weighted-sum function, the inventors have realised that the Lagrange multipliers found for the constrained objectives may be used for the weights. As a consequence, the optimal solution can be found in only one optimisation instead of many as in the 2pϵc method. We propose that the Lagrange multipliers found using a first image (e.g. a planning scan) and an optimisation method (e.g. ϵc or 2 pϵc methods) are then used with an inter-fraction image in order to create an updated treatment plan. For example, the Lagrange multipliers can be used as the weights in a weighted-sum function. By using these same Lagrange multipliers, an updated treatment plan of acceptable quality can be produced in a greatly reduced period of time compared to re-running a full 2pϵc optimization.

In one aspect, therefore, the present invention provides an optimization method of a fluence pattern, to be provided by a radiotherapy apparatus to a patient, wherein a first fluence pattern is calculated based on a first image of a treatment area of the patient and one or more geometric constraints of the radiotherapy apparatus, and wherein generation of the first fluence pattern involves the use of one or more Lagrange multipliers. The method comprises the steps of, after a period of treatment, obtaining a second image of the treatment area of the patient; and using the second image and said one or more Lagrange multipliers to generate a second fluence pattern.

The method may be performed largely by computer, and so a further aspect of the invention provides a computer program product for performing the above method.

BRIEF DESCRIPTION OF THE DRAWINGS

An embodiment of the present invention will now be described by way of example, with reference to the accompanying figures in which;

FIG. 1 is a flowchart of a method according to embodiments of the present invention.

DETAILED DESCRIPTION OF THE EMBODIMENTS

Once a physician has input a list of treatment parameters (e.g. targets for which radiation is to be maximised, targets for which radiation is to be minimised, etc), a proposed radiotherapy treatment plan is typically prepared by an automated process. This can then be reviewed by a physician to ensure that it meets the clinical needs of the patient; if necessary the physician can adjust the treatment parameters until an acceptable treatment plan is produced.

This process uses as one of its inputs a three-dimensional image of the region that will (or may) be irradiated, which has been segmented by manual or automated processes (or some mix of the two) in order to indicate whether a specific part of the image such as a voxel (i.e. a three-dimensional pixel) is either not part of the patient (i.e. free space), part of the tumour or other target to be irradiated, a non-sensitive healthy part of the patient, or a sensitive healthy part of the patient. Target regions are allocated a minimum dose that is to be delivered, determined by the clinical outcome that is desired. Sensitive regions (such as certain organs) are allocated a maximum dose that must not be exceeded, else irreparable damage may be caused to the patient. Non-sensitive areas such as skin, fat and muscle tissue do not have a specific upper limit but are subject to the general aim of the process which is to minimise the dose to healthy tissue.

In addition, the automated process is provided with details of the constraints imposed on the treatment process by the apparatus that is being used, as noted above.

These various factors and constraints are then expressed as mathematical functions, which enable the process to be automated as a constrained optimisation problem. There are various ways of doing so.

One approach is a weighted-sum optimisation. Thus, if x represents the treatment plan and $f_i(x)$, i=1, ..., n, represents the various doses delivered to various areas of the patient, then we can allocate weights $w_i$ to each of the doses and the problem becomes the minimisation of:

$$w_1 f_1(x) + w_2 f_2(x) + w_3 f_3(x) + \ldots + w_n f_n(x) \quad (1)$$

subject to: $g(x) \leqq c$ where $g(x)$ represents the constraints and c is a constant (say, 0).

The solution of this optimisation problem is known, and involves determining the various plans that minimise the weighted sum for varying combinations of weights, thereby building a database of plans. This is explained in the paper by Craft D and Bortfeld T, 2008 "*How many plans are needed in an IMRT multi-objective plan database?*", published in Phys. Med. Biol. 53, 2785-96). With appropriate tools, the user can then search through this database and select the best plan as described in Monz M, Küfer K H, Bortfeld T R and Thieke C 2008 "*Pareto Navigation—algorithmic foundation of interactive multi-criteria IMRT planning*", Phys. Med. Biol. 53, 985-98.

This does however produce a selection of plans that need to be chosen between. In addition, the repeated solving of the problem for different weights in order to build up the portfolio of possible plans is intrinsically inefficient.

A method that is sometimes preferred is the ϵ-constraint (ϵc) method set out in Haimes Y Y, Lasdon L S and Wismer D A (1971) "*On a bicriterion formulation of the problems of integrated system identification and system optimization*", IEEE Trans. Man Cybern. 1 296-7. A preferred form of this method is known as the 2p-ϵc method and is explained in various publications, including Wilkens, J. J., Alaly J. R., Zakarian K., Thorstad W. L. and Deasy J. O., 2007, "*IMRT treatment planning based on prioritizing prescription goals*", Phys. Med. Biol. 52 1675-92; Jee K-W, McShan D. L. and Fraas B. A., 2007, "*Lexicographic ordering: intuitive multi-criteria optimization for IMRT*", Phys. Med, Biol. 52 1845-61, and Breedveld S, Storchi P R M, Keijzer M, Heemink A W and Heijmen B J M, 2007, "*A novel approach to multi-criteria inverse planning for IMRT*", Phys. Med. Biol. 52 6339-53.

The ϵc method uses an image of the patient together with a set of criteria (objectives) in which each objective is optimized separately, and then constrained while optimizing other, lower-prioritized objectives. The extension to the ϵc method is known as the 2-phase ϵ-constraint optimization (2pϵc) method. In this method, an objective may be considered optimized in that it has reached a defined goal (e.g. radiation fluence incident on a sensitive region under a certain threshold value). The objective may not be optimal (e.g. the lowest possible radiation fluence incident on the sensitive region), but it is sufficient for the purposes of the radiotherapy treatment. This relaxation of the requirements for one or more objectives may allow other objectives to be better optimized than previously possible.

These ϵc methods involve the use of Lagrangian optimisation of the treatment plan, and are described in greater detail below. This is a mathematical optimisation technique which seeks to locate a minimum value of a function, subject to other constraints, and is therefore well suited to this context. It does however require a very large amount of computation, and thus whilst it produces good quality plans, the computation process takes a significant time.

Thus, all the available plan computation methods require a significant runtime—sometimes of several hours. The effect of this in practice is that clinicians often obtain a volume image of the patient, and then prepare a single plan from that image, which is then used for all fractions in the course of treatment. The plan must therefore cater for the range of small movements of the target that are to be expected over the fractionated treatment. To do so, the plan is designed to deliver a dose to a "planning target volume" (PTV), which is the "clinical target volume" (CTV)—i.e. the actual tumour—plus a margin around the tumour to allow for movement. This means that the irradiation of some healthy tissue around the CTV is inevitable; if this could be reduced then patient outcomes could be improved.

There is, however, insufficient time to re-run the plan optimisation based on a fresh recent image of the patient, such as one taken immediately before the next fraction, whichever of the above methods are used. However, we realised that a short-cut is possible.

Assuming that an initial plan is prepared by an $\epsilon c$ or 2 $p\epsilon c$ method, then a Lagrangian process will have been used in order to do so. Lagrangian optimisation seeks to optimise, for example, the function:

$$f(x) \quad (2)$$

subject to a constraint function:

$$g(x)=c \quad (3)$$

To do so, a composite function known as the "Lagrange function" ($\Lambda$) is derived:

$$\Lambda(x, \lambda)=f(x)+\lambda(g(x)-c) \quad (4)$$

In this function, $\lambda$ is a new variable known as the "Lagrange multiplier". We then locate "stationary points" of the Lagrange function, which are the points at which the gradient or slope of the function is zero. This can be done using well-known techniques of differential calculus or computational methods. The result is a fixed value (or values) of x and $\lambda$ at which the constraints are complied with and f(x) is minimised. Usually, $\lambda$ is of academic interest only.

If there are multiple constraints, then there may be multiple $\lambda$s, i.e.:

$$\Lambda(x, \lambda_1, \lambda_2, \ldots, \lambda_n)=f(x)+\lambda_1(g(x)-c)+ \lambda_2(g(x)-c)+\ldots+\lambda_n(g(x)-c) \quad (5)$$

The solution of this somewhat more complex problem, in turn, reveals values of x, $\lambda_1, \lambda_2, \ldots, \lambda_n$ at which the constraints are complied with and f(x) is minimised.

We realised that the structure of equation (5) is very similar to the structure of equation (1), i.e. the weighted sum optimisation problem. That approach could not be used between fractions as the repeated efforts to solve it with different possible weights took too long. According to the invention, therefore, we bypass this problem by preparing a first treatment plan using a Lagrange optimisation process, then retaining the Lagrange multipliers obtained in that process and employing them as the weights in a weighted optimisation process. That reduces the time required for the weighted optimisation process to a level that is an acceptable wait time for a patient between scanning and treatment.

Therefore, an initial treatment plan can be derived in a known manner, such as an $\epsilon c$ or $2p\epsilon c$ method. Then, for each subsequent fraction a fresh image can be prepared and a semi-fresh treatment plan derived using a weighted optimisation process that is limited to the use of weights corresponding to the Lagrange multipliers obtained when preparing the initial treatment plan.

The initial treatment plan can be used for the first fraction that is delivered. Alternatively, if (for example) there is a significant wait between the initial scan and the first fraction, then a fresh scan can be taken before the first fraction and the treatment plan can be re-calculated based on that scan.

Thus, the pattern of scans for a daily fractioned treatment program might be:

| Day | Scan | Plan | Method | Treatment |
|---|---|---|---|---|
| 1 | Yes | Initial | $\epsilon c$ or 2p$\epsilon c$ | Yes |
| 2 | Yes | Plan 2 | Weighted sum | Yes |
| 3 | Yes | Plan 3 | Weighted sum | Yes |
| ... | ... | ... | ... | ... |
| n | Yes | Plan n | Weighted sum | Yes |

Alternatively:

| Day | Scan | Plan | Method | Treatment |
|---|---|---|---|---|
| 0 | Yes | Initial | $\epsilon c$ or 2p$\epsilon c$ | No |
| 1 | Yes | Plan 1 | Weighted sum | Yes |
| 2 | Yes | Plan 2 | Weighted sum | Yes |
| ... | ... | ... | ... | ... |
| n | Yes | Plan n | Weighted sum | Yes |

In embodiments of the present invention, the radiation is delivered by an apparatus having a source of radiation (e.g. a linear accelerator) and a collimator (e.g. a multi-leaf collimator), both of which are mounted on a rotatable gantry. A patient support is movable along a translation axis parallel to the rotation axis of the gantry.

During treatment, a patient lies on the support while being irradiated by the source. The collimator acts on the radiation beam in a plane transverse thereto, to shape and direct the radiation as appropriate. The gantry rotates around the patient, to allow the radiation beam to access the patient from different directions. In addition, the patient support may move along the translation axis, to allow the radiation beam access to different regions of the patient displaced along the translational direction.

The treatment plan defines (or is interpreted by the radiotherapy system to define) a fluence pattern deliverable to the patient, and actioned by the system defined above. Thus, the treatment plan may dictate one or more of: the intensity of radiation delivered by the source; the shape and position of the collimator at different locations around the patient; the position and movement of the patient support; and the position and rotational velocity of the gantry.

FIG. 1 is a flowchart of a method in accordance with embodiments of the present invention.

In step 10, markers are implanted into a patient in or around the treatment area. Suitable markers are cylindrical gold markers having a cross-sectional area of 1 mm×5 mm, although alternative markers may be used. The markers do not move relative to the target region during treatment, and so may be used in subsequent images to compensate for inter-fraction movement of the target region within the patient.

In step 12, a planning computed tomography (CT) scan is obtained of the treatment area of the patient. The image contains at least a target region for radiotherapy (e.g. a tumour), and may also contain one or more regions that are especially sensitive to radiation (e.g. healthy organs, healthy tissue, etc). One skilled in the art will appreciate that alternative methods may be used to acquire the image, including magnetic resonance imaging for example.

In step 14, a treatment plan (i.e. a fluence pattern of radiation) is calculated using a constraint method (e.g. the ϵ-constraint or 2pϵc methods described below).

In addition to the medical constraints for adequate treatment (i.e. in which regions is radiation fluence to be maximized, and in which regions is radiation fluence to be minimized) the treatment plan takes into consideration one or more geometric constraints of the radiotherapy system itself. For example, such geometric constraints may include the maximum intensity of the source, the width of the collimator leaves, the maximum rotation speed of the gantry, etc.

The calculation of the first treatment plan generates one or more Lagrange multipliers that will be used later in the weighted-sum method. According to embodiments of the invention, therefore, these Lagrange multipliers are stored in a memory for later access.

The generation of the treatment plan in step 14 may take some considerable time, so it is not generally practical for the patient to remain in situ while the plan is calculated.

Some time later, in step 16, the patient presents for their first fraction of treatment, and a further CT image is obtained of the treatment area (although again alternative methods may be used to obtain the image).

In step 18, the markers inserted in step 10 are detected and compared with their location in the first image. If necessary, the second image is compensated for interfraction movement of the patient, e.g. translated such that the positions of the markers in the two images are aligned.

In step 20, according to the present invention, the second image (compensated for patient motion if necessary) is used in conjunction with the Lagrange multipliers to generate an updated treatment plan. The Lagrange multipliers are input as weights in a weighted-sum method to arrive at an acceptable treatment plan far quicker than previously possible. This aspect will be described in greater detail below.

In step 22, the patient is treated according to the second treatment plan, followed by a period of recovery in step 24. The length of the recovery period will of course be set by the medical practitioners in accordance with the requirements of each case; however, common recovery periods are approximately 24 hours. As discussed above, most radiotherapy treatment is delivered in a plurality of fractions. Thus, once recovered, the method repeats from step 16 onwards, with a new CT scan being taken before each fraction, and the treatment plan being updated in accordance with the present invention.

In the following, the weighted-sum, ϵ-constraint and 2pϵc methods are described in more detail. Each objective or constraint reflects the dose applied to structures within the treatment area, whether healthy or unhealthy. Objectives are denoted by $f_i$, $i \in \{1, K, n\}$, and the constraints by $g_j$, $j \in \{1, K, m\}$. For readability, the constraints are summarized in a vector $g(x)$, for which each element should be $\leq 0$. x represents proposed fluence patterns.

In the weighted-sum method, the objectives are weighted and summed together. Let the weights be denoted by $w = (w_1, K, w_n)$. The optimization problem to be solved becomes $$\text{minimize } w_1 f_1(x) + w_2 f_2(x) + K + w_n f_n(x)$$

$$\text{subject to } g(x) \leq 0 \quad (6)$$

This optimization problem may be solved for varying combinations of weights, building a database of plans. With appropriate tools, the user can search through this database and select the best plan. However, this can take some time to complete, and may require some human interaction to select an appropriate plan. Note that the sum of the weights does not necessarily have to be normalized to 1, but this is usually done because it displays the relative weights more clearly.

In contrast, the ϵ-constraint method optimizes one objective at a time while keeping the others constrained. (Similar methods are goal programming and lexicographic ordering.) This method optimizes each objective only once.

Thus, the method may be summarized by $$\text{minimize } f_1(x)$$

$$\text{subject to } g(x) \leq 0$$

where $f_1(x)$ is the objective with the highest priority. Once minimized, $f_1(x)$ is constrained to its minimal value and $f_2(x)$ calculated, where $f_2(x)$ is the objective with the second-highest priority. This process is repeated for each successively lower-priority objective until all objectives have been minimized as far as possible, bearing in mind the constrained higher-priority objectives.

To allow for more flexibility, this method may be extended in embodiments of the present invention to a 2-phase ϵ-constraint optimization (2pϵc), where a goal can be assigned to each objective. When it is possible to minimize the dose below a certain threshold (i.e. its goal) for one objective, it is often more desired to minimize the dose for other (lower priority) objectives first than to directly minimize the dose for the higher priority objectives to its fullest extent.

For example, if the minimum mean dose for a parotid gland drops below 26 Gy (e.g. 15 Gy), it can be considered spared. In the next step, the parotid is then limited to 26 Gy while minimizing the dose to a lower prioritized organ at risk (OAR) (e.g. the submandibular gland). Setting the constraint for the parotid higher than its minimum (to 26 Gy instead of 15 Gy) increases the probability of sparing the submandibular gland as well.

The objectives and their priorities and goals are given in a prioritized list, which may be called a wish list. Each priority contains an objective and a desired goal. So, for n objectives, objective $f_i(x)$ has priority i and goal $b_i$. Furthermore, the list may contain (hard) constraints $g(x)$ which are to be met at all times.

In the first iteration of the first phase, the objective having highest priority is optimized:

$$\text{minimize } f_i(x)$$

$$\text{subject to } g(x) \leq 0$$

Depending on the result x*, the new bound is chosen according to the following rule:

$$\varepsilon_i = \begin{cases} b_i & f_i(x^*)\delta \leq b_i \\ f_i(x^*)\delta & f_i(x^*)\delta \geq b_i \end{cases}$$

where δ is a slight relaxation to create some space for the subsequent optimizations, set to 1.03 (3%) in one embodiment. Note that this relaxation is not mandatory, but may prevent the optimization algorithm from stalling due to numerical problems. In other embodiments, a relaxation of $\delta = 1 + O(10^{-4})$ may be used, as this is often enough to prevent numerical problems; however, a relaxation of $\delta=1.03$ also prevents the solution from ending up in one of the end points of the Pareto curve.

The next optimization optimizes $f_2$, keeping $f_1$ constrained:

minimize $f_2(x)$ subject to $g(x) \leq 0$ $f_1(x) \leq \epsilon_1$

This is repeated for all n objectives.

In the second phase of the multi-criteria optimization, all objectives which met their goals are minimized to their fullest, while keeping all others constrained.

So, for each $f_i$ which met its goal $b_i$ solve, in order of priority:

minimize $f_i(x)$ subject to $g(x) \leq 0$ $f_k(x) \leq \epsilon_k, k \in \{1,K,n\} \setminus i$ and then set $\epsilon_i = f_i(x^*) \delta$.

Note that this second phase resembles the original $\epsilon$-constraint method, and therefore the solution of the 2p$\epsilon$c method has the same properties (i.e. Pareto optimality) as the $\epsilon$-constraint method.

The last iteration of an $\epsilon$-constraint problem solves the following problem (without loss of generality it can be assumed that the objective with priority n is the last one optimized on):

minimize $f_n(x)$ subject to $g(x) \leq 0$ $f_i(x) \leq \epsilon_i, i \in \{1,K,n-1\}$ \hfill (7)

As noted above, one way to solve a constrained problem is by rewriting the problem as an unconstrained optimization problem, which is called the Lagrangian. The Lagrangian for problem (7) is $$\Lambda(x, v, \lambda) = f_n(x) + \sum_{i=1}^{n-1} v_i(f_i(x) - \varepsilon_i) + \sum_{j=1}^{m} \lambda_j g_j(x)$$

which is to be minimized with respect to x, $v$ and $\lambda$, where $v$ and $\lambda$ are nonnegative vectors of Lagrange multipliers. A constraint is called active if its corresponding Lagrange multiplier is not equal to 0. As a result of the $\epsilon$-constraint optimization, all constrained objectives $f_i(x) \leq \epsilon_i$, $i \in \{1, K, n-1\}$, are active, so $v_i > 0$. (In this case, the Lagrange multipliers for the constrained objectives may also be termed Kuhn-Tucker multipliers.)

For finding the optimal triplet $(x^*, v^*, \lambda^*)$, many methods are available and would be familiar to those skilled in the art. One example of such a method is based on interior-point optimization (see, for example, "Primal-Dual Interior-Point Methods" by S J Wright, the contents of which are incorporated herein by reference).

According to embodiments of the present invention, the weights for the weighted-sum method may be chosen to be equal to the Lagrange multipliers for the constrained objectives from the last iteration of the E-constraint optimization, as this results in an identical optimal solution.

Proof.

Let $\Lambda_\varepsilon(x^*, v^*, \lambda^*)$ be the Lagrangian for the optimal solution of the final iteration of an $\epsilon$-constraint optimization (7):

$$\Lambda_\varepsilon(x^*, v^*, \lambda^*) = f_n(x^*) + \sum_{i=1}^{n-1} v_i^*(f_i(x^*) - \varepsilon_i) + \sum_{j=1}^{m} \lambda_j^* g_j(x^*).$$

Suppose the weights for the weighted-sum method (6) are chosen equal to $v_i^*$ and $w_n = 1$.

Then, the Lagrangian for the weighted-sum problem becomes $$\Lambda_w(x, \lambda) = f_n(x) + \sum_{i=1}^{n-1} v_i^* f_i(x) + \sum_{j=1}^{m} \lambda_j g_j(x).$$

Subtracting the constant $$\sum_{i=1}^{n-1} v_i^* \varepsilon_i$$

from $\Lambda_w$ does not change the optimal solution. Introduce $$\hat{\Lambda}_w(x, \lambda) = f_n(x) + \sum_{i=1}^{n-1} v_i^*(f_i(x) - \varepsilon_i) + \sum_{j=1}^{m} \lambda_j g_j(x)$$

and let $\hat{\Lambda}_w(\bar{x}, \bar{\lambda})$ be the optimal solution for $\hat{\Lambda}_w$.

The constraints $g(x)$ can be assumed to be linear independent. In this case, the set of Lagrange multipliers $\lambda$ is unique. Therefore, $\bar{\lambda} \equiv \lambda^*$. Because the Lagrangian $\hat{\Lambda}_w$ is convex in x ($\lambda$ and $v$ are fixed), it may be concluded that $\bar{x} \equiv x^*$. Thus, the Lagrange multipliers $v_i^*$ calculated during generation of the initial treatment plan, using either the $\epsilon$-constraint method or the 2p$\epsilon$c method, can be input as the weights $w_i$ in the weighted-sum method for updating the treatment plan in later fractions.

The present invention therefore provides a method for updating and optimizing a treatment plan for radiotherapy. An initial plan, calculated using a constraint-driven method, may be updated using a weighted-sum method, where Lagrange multipliers generated in the constraint method are reused as the weights in the weighted sum. This method results in acceptable updated treatment plans that are generated in a small fraction of the time taken to generate an entirely new treatment plan, reducing patient discomfort and ensuring the radiotherapy facility can treat more patients.

It will of course be understood that many variations may be made to the above-described embodiment without departing from the scope of the present invention.

Although the present invention has been described with reference to preferred embodiments, workers skilled in the art will recognize that changes may be made in form and detail without departing from the spirit and scope of the invention.

The invention claimed is:

1. An optimization method of a fluence pattern, to be provided by a radiotherapy apparatus to a patient, wherein a first fluence pattern is calculated based on a first image of a treatment area of the patient and one or more geometric constraints of the radiotherapy apparatus, and wherein generation of the first fluence pattern involves the calculation of one or more Lagrange multipliers, the method comprising:

after a period of treatment, obtaining a second image of the treatment area of the patient; and using the second image and said one or more Lagrange multipliers to generate a second fluence pattern.

2. The method as claimed in claim 1, wherein said one or more Lagrange multipliers are input as weights applied to one or more respective objectives in a weighted sum to generate said second fluence pattern.

3. The method as claimed in claim 2, wherein said first fluence pattern is obtained using a method in which one or more objectives are optimized at a time while other objectives are constrained.

4. The method as claimed in claim 3, wherein said one or more objectives are optimized to be below a threshold value.

5. The method as claimed in claim 1, wherein said first and second images comprise a target region and one or more regions adjacent the target region that are sensitive to radiation.

6. The method as claimed in claim 5, the first and second fluence patterns comprise instructions for delivery of radiation to the area of the patient, in which radiation is delivered to the target region at a first, relatively high, intensity, and radiation is delivered to the one or more sensitive regions at a second, relatively low, intensity.

7. The method as claimed in claim 2, wherein the radiotherapy apparatus comprises a source of radiation for generating a radiation beam, and a collimator for acting on the radiation beam in a plane transverse thereto, the source of radiation and the collimator being mounted on a rotatable gantry.

8. The method as claimed in claim 5, wherein the first and second fluence patterns comprise instructions for one or more of: the speed of rotation of the gantry; the intensity of the radiation beam; and the shape and position of the collimator with respect to the radiation beam.

9. The method as claimed in claim 2, further comprising:

implanting one or more markers in the area of the patient; and using said one or more markers to compensate for alteration of the patient's position in said first image and the patient's position in said second image.

10. The method as claimed in claim 2, wherein said first and second images are obtained using computed tomography.

11. An optimization method for a radiotherapy treatment plan, for delivery of a therapeutic dose of radiation by a radiotherapy apparatus to a patient, the method comprising:

obtaining a first image of an area of the patient, the area including at least a target region for a therapeutic dose of radiation, and one or more regions sensitive to radiation;

using the first image and one or more geometric constraints of the radiotherapy apparatus to generate a first treatment plan, in which radiation is delivered to the target region at a first, relatively high intensity, and radiation is delivered to the one or more sensitive regions at a second, relatively low intensity;

obtaining a second image of the area of the patient; and using the second image and one or more Lagrange multipliers found in the generation of the first treatment plan to form a second treatment plan.

12. A computer program product for optimizing a fluence pattern, to be provided by a radiotherapy apparatus to a patient, wherein a first fluence pattern is calculated based on a first image of a treatment area of the patient and one or more geometric constraints of the radiotherapy apparatus, and wherein generation of the first fluence pattern involves the calculation of one or more Lagrange multipliers, the computer program product comprising: a computer readable storage medium having a computer program stored thereon for performing the steps of:

receiving second image data of the treatment area of the patient; and using the second image and said one or more Lagrange multipliers to form a second fluence pattern.

* * * * *